United States Patent [19]

Thomas et al.

[11] Patent Number: 4,613,334

[45] Date of Patent: Sep. 23, 1986

[54] LIGHTFASTNESS OF DYEINGS OBTAINED WITH ACID DYES OR METAL COMPLEX DYES ON POLYAMIDES

[75] Inventors: Michael Thomas, Weisenheim; Peter Neumann, Wiesloch; Dieter Wegerle, Mannheim; Reinhold Krallmann, Weisenheim, all of Fed. Rep. of Germany

[73] Assignee: BASF Aktiengesellschaft, Rheinland-Pfalz, Fed. Rep. of Germany

[21] Appl. No.: 633,457

[22] Filed: Jul. 23, 1984

[30] Foreign Application Priority Data

Jul. 23, 1983 [DE] Fed. Rep. of Germany ....... 3326640

[51] Int. Cl.$^4$ .......................... D06P 1/64; D06P 3/24; D06P 5/10
[52] U.S. Cl. ............................................ 8/442; 8/599; 8/602; 8/624; 8/680; 8/685; 8/924
[58] Field of Search .................. 8/442, 599, 600, 602, 8/624

[56] References Cited

U.S. PATENT DOCUMENTS

| | | | |
|---|---|---|---|
| 3,203,752 | 8/1965 | Mills et al. | 8/551 |
| 3,361,710 | 1/1968 | Sparks | 524/204 |
| 3,363,969 | 1/1968 | Brooks | 8/493 |
| 3,993,772 | 11/1976 | Pommer et al. | 549/487 |
| 4,253,843 | 3/1981 | Bannigan | 8/442 |
| 4,383,835 | 5/1983 | Preuss et al. | 8/602 |
| 4,544,372 | 10/1985 | Heise et al. | 8/602 |

FOREIGN PATENT DOCUMENTS

| | | |
|---|---|---|
| 2625386 | 12/1977 | Fed. Rep. of Germany . |
| 3247051 | 6/1984 | Fed. Rep. of Germany . |
| 57-56590 | 4/1982 | Japan . |
| 1321645 | 6/1973 | United Kingdom . |
| 1392953 | 5/1975 | United Kingdom . |

*Primary Examiner*—A. Lionel Clingman
*Attorney, Agent, or Firm*—Oblon, Fisher, Spivak, McClelland & Maier

[57] ABSTRACT

A process for improving the lightfastness of dyeings obtained with acid dyes and/or metal complex dyes on polyamide textile materials, by treating the latter and 0.01–1% by weight of a copper hydroxamate before, during or after dyeing.

3 Claims, No Drawings

LIGHTFASTNESS OF DYEINGS OBTAINED WITH ACID DYES OR METAL COMPLEX DYES ON POLYAMIDES

To improve the lightfastness of dyed polyamides, the polyamide fibers or other textile structures are treated with water-soluble copper salts. However, the affinity of the copper salts for the textile structure is relatively low so that the dyehouse effluent is heavily contaminated with copper ions.

German Laid-Open Application DOS No. 3,041,153 discloses a process for improving the lightfastness of polyamide dyeings wherein polyamine fibers are treated, before, during or after dyeing, by means of copper complexes of the reaction products of salicylaldehydes with alkylamines, aromatic diamines or hydrazine and/or copper complexes of o-hydroxybenzophenones. It is true that the affinity of the organic copper complex compounds is substantially greater than that of the copper salts, but because of their pronounced intrinsic color complexes described in German Laid-Open Application DOS No. 3,041,153 have the disadvantage that, especially in the case of brilliant dyeings, they shift the hue and dull the dyeing to a greater or lesser extent.

It is an object of the present invention to provide materials for improving the lightfastness of dyeings obtained with acid dyes or metal complex dyes on polyamide, which possess good affinity for polyamide and have little or no adverse effect on the appearance of the dyeings, especially on their brilliance.

We have found that this object is achieved, according to the invention, by a process for improving the lightfastness of dyeings obtained with acid dyes and/or metal complex dyes on polyamide textile materials by treating the said materials with copper complexes, wherein copper hydroxamates are employed as the complexes.

The process according to the invention is used for dyeing textile materials of natural polyamides and of synthetic polyamides (nylons). The textile materials may, for example, be filaments, yarns, woven fabrics or nonwovens. Suitable nylons are condensates of dicarboxylic acids and diamines, and lactam polymers. The textile materials are treated with acid dyes and/or metal complex dyes by conventional dyeing methods. Acid dyes and metal complex dyes are commercially available and are described in detail in, for example, the Color Index.

The acid dyes contain one or more sulfo groups. Suitable metal complex dyes include 1:1 or, preferably, 1:2 complexes of chromium and cobalt. These may contain solubilizing groups or be free from such groups. Suitable phthalocyanine dyes include the conventional copper phthalocyanines and nickel phthalocyanines. Mixtures of acid dyes and metal complex dyes may also be used.

In order to improve the lightfastness of dyed nylons which are dyed with acid dyes and/or metal complex dyes, the textile materials are treated with copper hydroxamates. This treatment may be carried out before, during or after dyeing. The copper hydroxamates are employed in aqueous solution or, if they are sparingly water-soluble, in a dispersed form. Commercial products may be used for dispersing. Preferably, the dye bath contains one or more copper hydroxamates, which are employed in amounts of 0.01–1, preferably 0.05–0.3, % by weight, based on textile, depending on the molecular weight of the hydroxamate. Any of the copper hydroxamates may be used to improve the lightfastness. The copper hydroxamates are prepared by, for example, reacting a carboxylic acid chloride and hydroxylamine or a hydroxylamine derivative in the presence of a base to give a hydroxamic acid, which is then converted to the corresponding copper hydroxamate by treatment with an inorganic copper salt, for example copper sulfate or copper chloride. One mole of copper salt is reacted with 2 moles of a hydroxamic acid, or alkali metal salt thereof. The preparation of hydroxamic acids is disclosed in, for example, German Laid-Open Application DOS No. 2,455,082.

Examples of copper hydroxamates to be used according to the invention are compounds of the formula

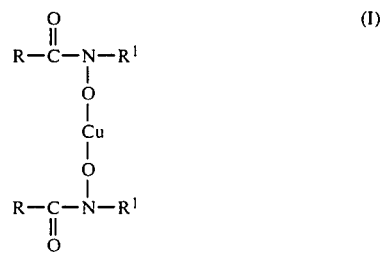

where

R is $C_1$–$C_{17}$-alkyl, or $C_3$–$C_8$-cycloalkyl which is unsubstituted or substituted by one or two alkyls of 1 to 4 carbon atoms,

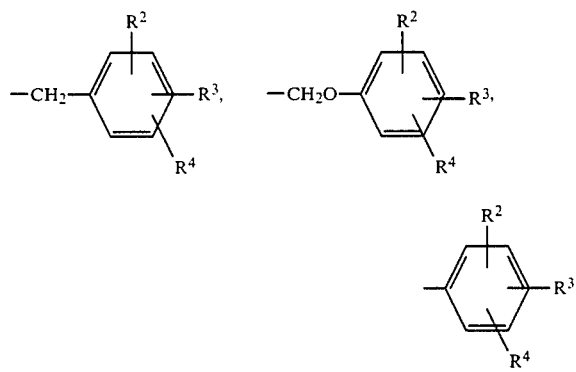

or substituted or unsubstituted furanyl, thiophenyl or pyridinyl, $R^2$, $R^3$ and $R^4$ are hydrogen, $C_1$–$C_4$-alkyl, methoxy or ethoxy, or one or two of the radicals $R^2$, $R^3$ and $R^4$ are chlorine or bromine and $R^1$ is hydrogen, $C_1$–$C_{12}$-alkyl, $C_3$–$C_8$-cycloalkyl or

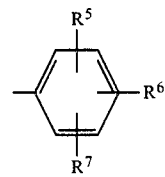

where $R^5$, $R^6$ and $R^7$ are hydrogen, $C_1$–$C_4$-alkyl or methoxy.

Preferred copper hydroxamates of the formula I are those where

R is $C_1$–$C_8$-alkyl, cyclohexyl,

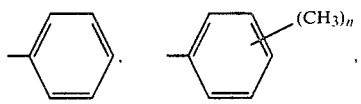

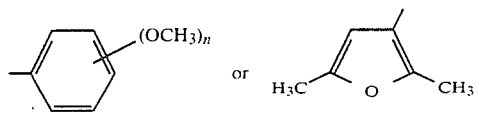

n is 1–3 and
$R^1$ is methyl, cyclohexyl or phenyl.

Examples of radicals R are:

$C_1$–$C_{17}$-alkyl, eg. methyl, ethyl, n-propyl, isopropyl, n-butyl, iso-butyl, sec.-butyl, tert.-butyl, n-pentyl, 3-methylbutyl, 1-ethylpropyl, 1,1-dimethylpropyl, 2,2-diimethylpropyl, n-hexyl, n-heptyl, 1-ethylpentyl, n-octyl, 2,4,4-trimethylpentyl, n-nonyl, n-decyl, n-undecyl, n-tridecyl, n-pentadecyl and n-heptadecyl, $C_3$–$C_8$-cycloalkyl, eg. cyclopropyl, cyclobutyl, cyclopentyl, cyclohexyl, 4-methylcyclohexyl, 4-tert.-butylcyclohexyl, 3,5-dimethylcyclohexyl, cycloheptyl and cyclooctyl, radicals of the formula

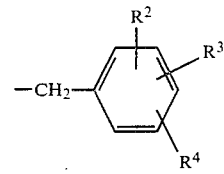

eg. benzyl, 2-, 3- and 4-methylbenzyl, 4-ethylbenzyl, 4-isopropylbenzyl, 4-tert.-butylbenzyl, 2-, 3- and 4-chlorobenzyl, 2-, 3- and 4-bromobenzyl, 2-, 3- and 4-methoxybenzyl, 2-, 3- and 4-ethoxybenzyl, 3,4-dimethoxybenzyl, 3,5-dimethoxybenzyl and 3,4,5-trimethoxybenzyl, radicals of the formula

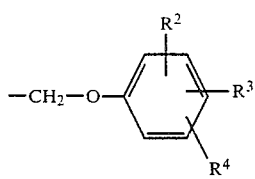

eg. phenoxymethyl, 2-, 3- and 4-methylphenoxymethyl, 2-, 3- and 4-ethylphenoxymethyl, 4-isopropylphenoxymethyl, 4-n-butylphenoxymethyl, 4-tert.-butylphenoxymethyl, 2,3-dimethylphenoxymethyl, 2,4-dimethylphenoxymethyl, 2,5-dimethylphenoxymethyl, 3,5-dimethylphenoxymethyl, 3,4-dimethylphenoxymethyl, 2-methyl-4-tert.-butyl-phenoxymethyl, 3,4,5-trimethoxyphenoxymethyl, 2,4,6-trimethylphenoxymethyl, 2,6-dimethyl-4-tert.-butylphenoxymethyl, 2-, 3- and 4-chlorophenoxymethyl, 2-, 3- and 4-bromophenoxymethyl, 2-, 3- and 4-methoxyphenoxymethyl, 4-ethoxyphenoxymethyl and 2-methyl-4-chlorophenoxymethyl, radicals of the formula

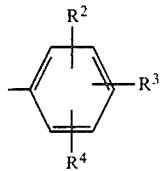

eg. phenyl, 2-, 3- and 4-methylphenyl, 2-, 3- and 4-ethylphenyl, 2-, 3- and 4-n- or iso-propylphenyl, 2-, 3- and 4-n or tert.-butylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 2,4-dimethyl-6-tert.-butylphenyl, 2-, 3- or 4-chlorophenyl, 2-, 3-bromophenyl, 2,4-dichlorophenyl, 2,5-dichlorophenyl, 2,6-dichlorophenyl, 3,5-dichlorophenyl, 2-, 3- and 4-methoxyphenyl, 2,3-dimethoxyphenyl, 2,4-dimethoxyphenyl, 2,6-dimethoxyphenyl, 3,4-dimethoxyphenyl, 3,5-dimethoxyphenyl, 2-ethoxyphenyl, 4-ethoxyphenyl, 2,3,4-trimethoxyphenyl and 3,4,5-trimethoxyphenyl, fur-2-yl, fur-3-yl, 2,5-dimethylfur-3-yl, thien-2-yl, thien-3-yl, pyrid-2-yl, pyrid-3-yl, pyrid-4-yl and 2-chloropyrid-3-yl.

Preferably, R is methyl, ethyl, n-propyl, isopropyl, n-butyl, iso-butyl, sec.-butyl, tert.-butyl, n-pentyl, 2,2-dimethylpropyl, n-hexyl, n-heptyl, 1-ethylpentyl, 2,4,4-trimethylpentyl, cyclohexyl, benzyl, phenoxymethyl, phenyl, 2-, 3- and 4-methylphenyl, 2,4,6-trimethylphenyl, 4-methoxyphenyl, 3,4,5-trimethoxyphenyl or 2,5-dimethyl-fur-3-yl.

Examples of the radicals $R^1$, in addition to hydrogen and the $C_1$–$C_{12}$-alkyl radicals mentioned for R, are cyclohexyl, phenyl, 2-, 3- and 4-methylphenyl, 2,3-dimethylphenyl, 2,4-dimethylphenyl, 2,5-dimethylphenyl, 2,6-dimethylphenyl, 3,5-dimethylphenyl, 2,4,6-trimethylphenyl, 2-ethylphenyl, 4-ethylphenyl, 4-n-propylphenyl, 4-isopropylphenyl, 4-n-butylphenyl, 4-tert.-butylphenyl, 2,6-dimethyl-4-tert.-butylphenyl, 2,4-diisopropylphenyl, 2,4,6-triisopropylphenyl, 2-, 3- and 4-methoxyphenyl, 2,4-dimethoxyphenyl, 2-methyl-4-methoxyphenyl and 3,4,5-trimethoxyphenyl.

Preferred radicals $R^1$ are methyl, cyclohexyl and phenyl.

The degree of fixing of the copper hydroxamates to the polyamide textile materials is—as with other, conventional copper complexes—relatively high (about 50% of the complex compounds contained in the dye liquor are fixed to the textile material, while the degree of fixing of inorganic copper compounds on polyamides is at most 15%). Using the copper hydroxamates it is possible to produce brilliant dyeings on polyamides, virtually without dulling of the hue.

In the Examples, parts are by weight.

Preparation of copper hydroxamates (a) A warm solution of 18.75 parts of copper-II chloride dihydrate in 50 parts of ethanol is added over 15 minutes to 27.54 parts of potassium N-cyclohexyl-2,5-dimethylfuran-3-hydroxamate in 50 parts of ethanol at 40°–50° C. The mixture is then stirred for 4 hours at the same temperature. Thereafter the precipitated potassium chloride is filtered off hot and the filtrate is concentrated under reduced pressure to half its volume. On cooling the thus concentrated filtrate, crystals separate out and these are filtered off and dried. 25.5 parts of the copper salt of the formula

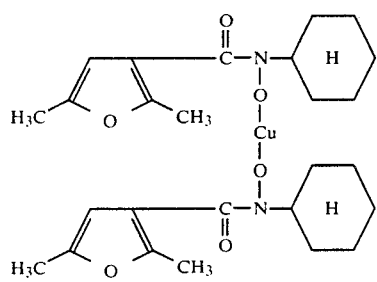  (II)

having a melting point of 125°–130° C., are obtained.

Using the same procedure, the potassium hydroxamates shown in the Table, under (b) to (h), are reacted with copper-II dichloride dihydrate to give the corresponding copper hydroxamates. The parts of copper hydroxamate obtained from the reaction, and the melting points of the product, are also shown in the Table.

TABLE

| Parts of potassium hydroxamate | | Parts of copper hydroxamate | Melting point (°C.) |
|---|---|---|---|
| (b) 26.94 | ![structure] | 23.3 | 65–67 |
| (c) 25.74 | ![structure] | 23.0 | 122–125 |
| (d) 27.14 | ![structure] | 24.8 | 152–156 |
| (e) 29.95 | ![structure] | 28.1 | 235–240 |
| (f) 26.34 | ![structure] | 22.4 | 89–92 |
| (g) 23.74 | ![structure] | 19.1 | 102–105 |
| (h) 18.93 | ![structure] | 16.0 | 204–208 |

EXAMPLE 1

100 parts of a polyamide yarn are dyed in a bath which contains 200 parts of water, 0.7 part of the yellow dye of the formula

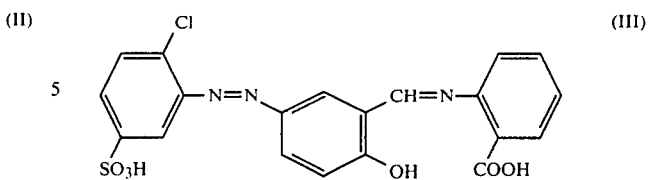  (III)

in the form of the 1:2 chromium complex, 0.3 part of the reddish violet dye of the formula

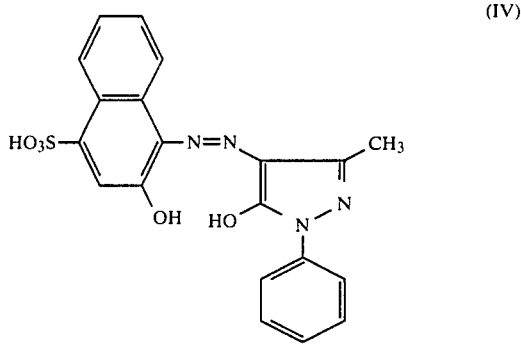  (IV)

also in the form of the 1:2 chromium complex, 0.5 part of the reaction product of 1 mole of oleylamine with 12 moles of ethylene oxide, and 0.1 part of the copper complex defined under (a) above. The pH of the bath is set to 5.0 by adding acetic acid, and the polyamide yarn is dyed for 60 minutes at the boil. It is then rinsed thoroughly. An orange brown dyeing is obtained, which has markedly improved lightfastness compared to a dyeing obtained without addition of compound (a).

EXAMPLE 2

100 parts of a polyamide fabric are dyed for 40 minutes at 115° C. in an autoclave, using a bath, at pH 5.0, which contains 0.7 part of the yellow dye of the formula III as the 1:2 chromium complex, 0.3 part of the reddish violet dye of the formula IV as the 1:2 chromium complex and 0.5 part of the reaction product of 1 mole of oleylamine with 12 moles of ethylene oxide. After dyeing, the fabric is rinsed, dried and subsequently impregnated, on a padder, with a bath containing 1 g of the copper complex (a) per liter of water, the wet pick-up being 100% by weight. The fabric thus impregnated is dried and treated with hot air at 190° C. for 20 seconds. An orange brown dyeing is obtained, the lightfastness of which is markedly improved over that of a dyeing which has not been after-treated.

The further compounds (b) to (h) shown as Examples in the Table give similar improvements in lightfastness to that achieved with copper complex (a).

EXAMPLE 3

The polyamide yarn mentioned in Example 1 is dyed at the boil in an aqueous bath, at pH 5.0, using 1%, based on yarn weight, of the copper phthalocyanine dye Color Index No. 74180, in the presence of 0.1% of copper complex (a). A brilliant deep blue dyeing is obtained.

COMPARATIVE EXAMPLE 1

Example 3 is repeated, except that in place of the copper complex (a) the copper complex of the formula

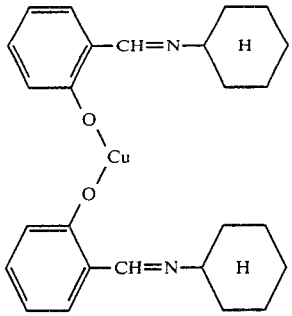

(according to German Laid-Open Application DOS No. 3,041,153, Example 1(a) is used, in an amount of 0.1%. A turquoise dyeing is obtained, the hue being markedly shifted toward green and dulled.

We claim:

1. A process for improving the lightfastness of dyeings obtained from acid dyes or metal complex dyes or a mixture thereof on polyamide textile materials by treating the materials, before, during or after dyeing, with at least one copper hydroxamate complex of the formula:

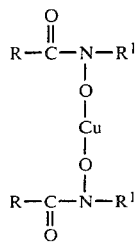

wherein R is $C_1$–$C_8$ alkyl, cyclohexyl or a radical of the formula

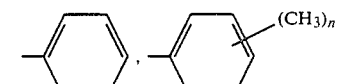

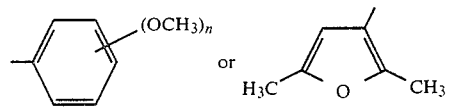

wherein n is 1 to 3; and $R^1$ is methyl, cyclohexyl or phenyl.

2. The process as claimed in claim 1, wherein the copper hydroxamate is employed in an amount of 0.01–1% by weight, based on the textile material.

3. The process as claimed in claim 2, wherein said copper hydroxamate is employed in an amount of 0.05–0.3 wt%.

* * * * *